United States Patent [19]

Cunningham et al.

[11] 4,305,798

[45] Dec. 15, 1981

[54] METHOD OF PREPARATIVE, KOHLRAUSCH-REGULATED ELECTROPHORESIS USING POLYETHYLENE GLYCOL DERIVATIZED TRAILING IONS

[75] Inventors: Bryce A. Cunningham, 400 Oakdale Dr., Manhattan, Kans. 66502; David L. Roerig, New Berlin, Wis.

[73] Assignee: Bryce Allen Cunningham, Manhattan, Kans.

[21] Appl. No.: 139,455

[22] Filed: Apr. 11, 1980

[51] Int. Cl.$^3$ ............................................. G01N 27/26
[52] U.S. Cl. ........................... 204/180 G; 204/180 R; 204/180 S; 23/230 B; 23/902; 23/912
[58] Field of Search ........... 204/180 G, 180 R, 180 S, 204/299 R; 424/12; 23/230 B, 902, 912

[56] References Cited

U.S. PATENT DOCUMENTS 3,686,087 8/1972 Vestermark ................ 204/180 G X
3,692,654 9/1972 Svendsen ................... 204/180 G X

*Primary Examiner*—Arthur C. Prescott
*Attorney, Agent, or Firm*—Schmidt, Johnson, Hovey & Williams

[57] ABSTRACT

An improved method of Kohlrausch-regulated electrophoresis (isotachophoresis) is disclosed for the preparative separation of respective macromolecular components such as proteins in a crude sample. The preferred method involves use of a substantially linear, polyethylene glycol derivatized trailing ion having a relatively high mass to charge ratio and a low mobility which is substantially independent of pH changes over a relatively broad pH range. The most preferred trailing ion is a polyethylene glycol dicarboxylic acid having a molecular weight of about 6,000–7,500, a pKa value of about 3.7, and a fully ionized mobility of about $-1.3 \times 10^{-5}$ cm.$^2$/volt/sec. The method hereof permits large scale protein separations and subsequent collection of purified protein fractions over a wide range of pH conditions and without interfering reactions between the proteins and trailing ion.

8 Claims, No Drawings

METHOD OF PREPARATIVE, KOHLRAUSCH-REGULATED ELECTROPHORESIS USING POLYETHYLENE GLYCOL DERIVATIZED TRAILING IONS

BACKGROUND OF THE INVENTION

The present invention is concerned with an improved method of electrophoresis especially designed for separation of macromolecules such as proteins or nucleic acids. More particularly, it is concerned with an electrophoretic method which is regulated by the Kohlrausch function and which is greatly improved by provision of specialized, high mass to charge ratio trailing ions, i.e., non-aromatic, acyclic, substantially linear, at least partially water dispersible polymers which are compatible with the macromolecular components to be separated, contain recurring ethylene oxide groups and at least one terminal group which is charge-bearing during the electrophoresis process, and which have mobilities substantially independent of pH over a range of at least about 4 pH units.

DESCRIPTION OF THE PRIOR ART

Electrophoresis can be broadly defined as the phenomenon of migration of suspended solid, liquid or gaseous charged particles to one of two electrodes (either the anode or cathode) under the influence of an external electromotive force. Electrophoretic ion migration was first reported in 1809, and since that time the theoretical and practical aspects and utility of electrophoresis have been extensively studied.

In 1897 Kohlrausch described the conditions for a stable moving boundary electrophoretic process. This work was the basis for the well-known Kohlrausch regulating function which is an equation describing the relationship between the transference numbers and concentrations of faster moving and slower moving ions in a stable moving boundary system. For the general case with multiple boundaries in a system containing a number of ions of different mobilities, the following equation is applicable:

$$\frac{T_f}{c_f} = \frac{T_{s1}}{c_{s1}} = \frac{T_{s2}}{C_{s2}} = \ldots \frac{T_{sn}}{c_{sn}} = \text{constant}$$

where $T_f$ is equal to the transference number of the fastest moving ion, and $c_f$ is the concentration of this ion. $T_{s1}, T_{s2}, \ldots T_{sn}$ respectively are the transference numbers of the next slowest moving ions in the series, whereas $c_{s1}, c_{s2} \ldots c_{sn}$ are respectively the corresponding concentrations of the slower moving ions.

Since the transference number of each successively slower ion is less than the transference number of its next adjacent leading ion, concentrations of trailing ion components are decreased as compared with their leading ions. In a system of several ionic components, an applied electric field will produce multiple boundaries with each component of a different transference number restricted to a respective band, and with the band being bounded by a leading and a trailing ion. At a given pH the ionic strength and transference number of all components can be considered constant so that the concentration in each band is controlled by the concentration of the leading ion. It is possible therefore to vary the concentration of each band by varying the concentration of the fastest moving ion.

The Kohlrausch regulating function was first applied for the analytical separation of protein components in a crude protein mixture in the work of Ornstein and Davis in the early 1960's. In the Ornstein-Davis method, an electrophoresis column is packed with polyacrylamide gel to which is applied a leading ion solution of relatively high mobility (such as chloride ion), followed by a crude protein mixture to be separated, and finally a layer of amphoteric trailing ions such as glycine. An applied electric field across the column caused electrophoretic migration of the ionic components, which will be regulated according to the Kohlrausch function. The protein components in the crude mixture having different mobilities will therefore be aligned and concentrated into discrete bands or discs in the column; for this reason, the Ornstein-Davis method is often referred to as "disc electrophoresis."

The Ornstein-Davis work sparked considerable interest in the area of electrophoretic separation of proteins. Out of this work a number of terms were coined to describe the Kohlrausch-regulated systems in question, e.g., isotachophoresis, ion migration, moving boundary, displacement electrophoresis, steady-state stacking and ionophoresis. Although most commentators prefer the term isotachophoresis, it is believed that a more appropriate general term is Kohlrausch regulated electrophoresis.

As those skilled in the art will readily appreciate, in order to establish the necessary conditions for Kohlrausch-regulated electrophoresis, the leading and trailing ions must be carefully selected. That is to say, the leading ion must have a mobility greater than that of any of the components to be separated, whereas the latter must have mobilities greater than that of the trailing ion. In the case of protein separations, it is also important that neither of the ions react with the protein itself. The selection of a leading ion generally presents no problems. For example, chloride is an excellent leading ion for a system in which protein components to be separated are anionic in character, whereas potassium ion is usually the best choice for cationic proteins.

The trailing ion however presents a number of significant problems. First, inasmuch as the trailing ion must have a mobility lower than that of any of the protein components, and since proteins often exhibit very low mobilities, the choice of ions is restricted at the outset. In the Ornstein-Davis method, the amphoteric molecule glycine was selected which has a mobility dependent upon pH. Thus, at the proper pH, glycine has a mobility less than that of most proteins to be separated.

There are two main disadvantages in the use of trailing ions having pH dependent mobilities. First, pH changes during electrophoresis will affect trailing ion mobility, usually increasing it, and this will in time destroy the Kohlrausch condition. If the mobility of an amino acid for example is made low enough to function as a trailing ion, it must usually be at a pH more than one unit away from its pK. It then has a very low buffer capacity and is all the more susceptible to pH changes during electrophoresis. A second objection to the use of amino acids or other amphoteric trailing ions is that strict limits are imposed on sample pH, else the proper mobility within the trailing ion cannot be obtained.

The above objections are less important in analytical disc gel electrophoresis systems because only relatively short distances and times are involved and significant pH changes are unlikely. In so-called preparative electrophoresis however where significant quantities of samples are separated and ultimately collected, longer migration distances and times are involved, and therefore pH changes may occur which will destroy the effectiveness of the amphoteric substances as trailing ions.

Accordingly, there is a real and heretofore unsatisfied need in the art for a method of electrophoresis which is improved by provision of a trailing ion having a relatively low mobility (less than that of most protein samples), which is substantially independent of pH over a significant range of pH units, e.g., at least about 4 units.

SUMMARY OF THE INVENTION

A greatly improved method of Kohlrausch-regulated electrophoresis is provided by the present invention which is particularly useful for separation of mixtures containing at least two (and usually many more) macromolecular components. The method hereof is adapted for preparative procedures, i.e., where respective purified samples are recovered. The methods hereof show particular utility in connection with separation of protein from crude mixtures thereof.

In the method, a crude mixture containing a plurality of macromolecular components is placed in a layer between a pair of physically distinct separate layers respectively including a leading ion and a trailing ion. The mobility of the leading ion is greater than that of the macromolecular components, whereas the mobility of the trailing ion is less than that of the components. A direct current is then passed through the respective layers to effect separation of the components in accordance with the Kohlrausch-regulating function. The specific improvement of the present invention comprises employing as the trailing ion a non-aromatic, acyclic, substantially linear, at least partially water dispersible polymer which is compatible with the macromolecular components. The polymer further includes recurring ethylene oxide groups and at least one terminal group (such as a carboxyl) which is charge-bearing during the passage of direct current through the distinct layers. Finally, the mobility of the polymer should be substantially independent of pH over a range of at least 4 pH units.

In particularly preferred forms, the trailing ion polymers in accordance with the invention should have a mass to charge ratio when fully ionized which is greater than that of the macromolecular components to be separated. In the case of protein separations, the mass to charge ratio is advantageously at least about 3,000 to 1.

Although a variety of particular polymers can be used to good effect in the invention, outstanding results have been achieved with polyethylene glycol derivatized polymers. These materials have the advantage of being readily obtainable, and will not react adversely with most protein components.

DESCRIPTION OF THE PREFERRED EMBODIMENTS

The non-aromatic, acyclic, substantially linear, at least partially water dispersible (at least about 10% w/v) polymer trailing ions in accordance with the invention are preferably of the formula $$X\text{+}O-CH_2-CH_2-O\text{+}CH_2CH_2-O)_{n_1}CH_2CH_2-O]\text{-}Y$$

wherein X and Y are respectively selected from the group consisting of:

(a) organic substituents having up to six carbon atoms and terminating in a carboxyl group;
(b) loweralkyl substituents having from 1 to 4 carbon atoms;
(c) substituents of the formula

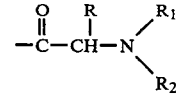

wherein R is an α amino acid side chain, $R_1$ is hydrogen or a loweralkyl having from 1 to 4 carbon atoms, inclusive, and $R_2$ is hydrogen, an amino acid or peptide;

(d) substituents of the formula

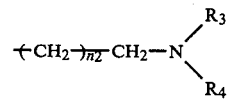

wherein $n_2$ is from 0 to 4, inclusive, and $R_3$ and $R_4$ are respectively taken from the group consisting of hydrogen and loweralkyl groups having from 1 to 4 carbon atoms, inclusive;

(e) substituents of the formula

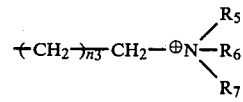

wherein $n_3$ is from 1 to 4, inclusive, $R_5$, $R_6$ and $R_7$ are respectively taken from the group consisting of hydrogen and loweralkyl groups having from 1 to 4 carbon atoms, inclusive;

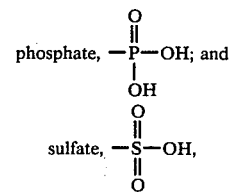

at least one of said X and Y being charge-bearing during said current passage,
and wherein $n_1$ is sufficiently large to give the polymer a mass to charge ratio when fully ionized which is greater than that of said components to be separated.

More preferably, at least one of the X and Y substituents illustrated are of the formula

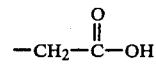

and $n_1$ ranges from about 100 to 150.

It has further been determined that polymers in accordance with the invention should have an absolute value mobility of up to about $1.3 \times 10^{-5}$ cm.$^2$/volt/sec. when fully ionized, although in accordance with the Kohlrausch-regulating function the mobility of the trailing ion need only be less than that of all of the components to be separated in a given electrophoretic system. In the case of anionic trailing ions, the mobility would have a negative sign, and conversely with cationic trailing ions the sign is positive.

The following examples will illustrate the methods of the present invention in the separation of crude protein samples into substantially purified fractions, followed by recovery of the samples for further studies and the like. It is to be understood in this respect that the examples are illustrative in nature, and nothing therein should be taken as a limitation upon the overall scope of the invention.

EXAMPLE 1

This example illustrates the preparative fractionation of horse serum into purified proteinaceous components.

Preparation of Horse Serum

Freshly drawn horse blood was allowed to clot at room temperature. After the clot had formed and partially retracted, the fresh serum was decanted. The remaining clot was then shaken and centrifuged at 10,000×g for 15 minutes to remove red cells and also to intentionally produce a reddish serum (from red cell damage). The reddish serum was dialyzed for 12 hours against 15% (w/v) sucrose containing a buffer of 0.05 M HCl adjusted to pH 8.5 with tris-hydroxymethylaminomethane (hereinafter referred to as "tris").

Preparation of Leading Ion

The leading ion solution is buffered and is prepared by initially making a 0.05 M hydrochloric acid solution in distilled water. Tris is then added to the HCl solution (with monitoring via a pH meter) until a pH of 8.5 is reached.

Preparation of Trailing Ion

A polyethylene glycol derivatized trailing ion (polyethylene glycol dicarboxylic acid) was synthesized by dissolving 130 grams of polyethylene glycol 6,000 (Baker Chemical Co.) having a molecular weight of about 6,000–7,500 in one liter of acetone. Jones reagent (28 ml.) was added to the dissolved mixture over a period of three hours with stirring at 30° C. The resulting dark green mixture was filtered through a celite pad, basified with 40 ml. of 2 Normal NaOH, transferred to 250 ml. centrifuge bottles, and cooled to −20° C. The oxidized polyethylene glycol (insoluble in cold acetone) was collected by centrifugation at 10,000×g for 10 minutes. The precipitate was redissolved in one liter of acetone to which 25 ml. of water had been added and the cooling and centrifugation process was repeated. If any greenish tinge remained in the product, precipitation was repeated a third time. The resultant product was dried in vacuo to a fine, white powder. Average yield was 70%.

The Jones reagent was prepared by adding 140 ml. of concentrated $H_2SO_4$ to a solution of 175 grams chromic anhydride in 500 ml. of distilled water. The resulting reagent was 8 N in oxygen. Jones reagent is commonly used to titrate alcohols dissolved in acetone, because it gives quantitative conversion to the carboxylic acid.

The final solution of trailing ion used in the present example was prepared by adding the polyethylene glycol dicarboxylic acid to distilled water (10% w/v), followed by buffering with tris to a pH of 8.5.

The polyethylene glycol dicarboxylic acid trailing ion polymer has a pKa of about 3.7, and is fully ionized above a pH of about 5, so that at the 8.5 pH range selected it is fully ionized. At this pH the polymer has a mass to charge ratio of about 3300 to 1. The mobility of the polymer (measured at pH 7.0, ionic strength 0.05 at 0° C.) is $-1.30 \times 10^{-5}$ cm.$^2$/volt/sec., and was determined to be substantially constant from basic pH down to about pH 5.0, whereupon the mobility decreases as expected by virtue of protonation of the terminal carboxylic groups. However, the mobility of the trailing ion polymer is substantially independent of pH over a relatively broad range of pH units.

Apparatus Set-Up

Broadly speaking, the electrophoresis apparatus used in this experiment included an upright, central plexiglass column (½ in. ID, ⅝ in. OD and 7¾ in. length), with an upper circular reservoir dish (4 in ID, 3 in. sidewall height), and with a similarly configured lowermost reservoir dish. Respective electrodes were placed in the dishes during operation, and a dialysis membrane and elution chamber are provided adjacent the lowermost end of the column. With the use of apparatus of this type, the horse serum can be separated into a plurality of proteinaceous components, followed by recovery of the respective components.

In more detail, a first annular plate (¼ in. thick, 2 in. diameter, and with a central opening of about ⅝ in.) is affixed to the bottom of the electrophoresis column, whereupon a 400 mesh screen is placed over the bottom end of the column and held in place by an O-ring. The underside of the first plate is then greased with silicone grease, whereupon an annular elution chamber is affixed to the underside of the first plate by means of nylon screws. The elution chamber has dimensions similar to that of the first plate, and is placed in register with the latter. In addition, the elution chamber includes respective inlet and outlet passageways which are tangentially oriented relative to the central opening therethrough. The passageways in turn are secured to corresponding lengths of tygon tubing for conveying elution material to the central elution chamber opening, and for conveying the material and eluted protein fractions away from the column.

A conventional dialysis membrane is next placed against the underside of the elution chamber in covering relationship to the central opening, followed by an annular reinforcement plate (⅛ in. thickness, 2 in. diameter, ⅝ in. central opening) and an outlet plate (¼ in. thickness, 2 in. diameter, ⅝ in. central opening). A depending delivery tube is affixed to the central opening of the outlet plate. Also, a pair of nylon screws are used to secure the dialysis membrane and two lowermost plates to the underside of the elution chamber.

The electrophoresis column is next filled by preparing a slurry of Sephadex G-50 (a cross linked polysaccharide conventionally used as an anti-convection medium in electrophoresis columns) and a quantity of the leading ion buffer solution. The elution chamber tubes are clamped off, and the slurry is poured into the column to a level of about half way up the column. The slurry is then allowed to settle until the solid material is in a relatively compact mass, which will take approximately one hour. At this point one of the elution chamber tubes is opened and excess liquid is drained from the column down to the level of the Sephadex bed, whereupon the tube is again clamped off.

The next step is to fill the lower reservoir dish with leading ion solution described above, followed by lowering the column until the tubular outlet is within the leading ion solution. A circular platinum electrode is then placed within the bottom reservoir (which will become the anode in the reaction).

The packed column is then loaded with an amount of the prepared horse serum sufficient to provide a total of 50 milligrams of protein to the column. The serum was carefully applied to the upper surface of the bed, using a pipette.

The trailing ion solution was thereafter layered over the serum sample, again using a pipette. Sufficient trailing ion solution was employed to fill the column and to partially fill the upper reservoir attached thereto.

A circular platinum cathode was then placed within the trailing ion solution in the upper reservoir, and the anode and cathode were connected to a Buchler D.C. power supply.

The inlet hose leading to the elution chamber is attached through a peristaltic pump to a supply of leading ion solution, which serves as an elution medium. The outlet hose from the elution chamber leads to a collection site having a plurality of fraction-collecting tubes.

The D.C. supply was then switched on to apply 100 volts D.C., 3 milliamps, across the column, in order to initiate electrophoresis. At this point migration of layers commenced and continued until a "steady state" condition was achieved, i.e., when all of the protein components to be ultimately separated were in respective zones or bands within the column in accordance with the Kohlrausch regulating function. Once steady state conditions were achieved, the migration of the layers continued down the column (at a rate determined by the migration of the leading ion) towards the elution chamber. During steady state conditions, the boundary between the leading ion and fastest moving protein band was visually observable, because the protein band exhibited a bright yellow color. Above the yellow band was a clear band, and atop this was a reddish colored band.

As the yellow leading band approached the elution chamber, a pulse-type elution was performed. Specifically, the outlet hose was unclamped, the pump started, leading ion solution was pumped through the chamber, and a solution fraction (0.4 ml.) recovered in a fraction-collecting tube. The pump was then shut off. The elution schedule was 5 seconds with pump on, followed by 1 minute, 55 seconds pump off. A total of 70 fractions was collected in this manner.

The fractions were then examined for protein content, esterase activity, and enzyme staining pattern (the latter by disc electrophoresis). The results of these tests showed that separation of the two esterases (aryl and choline) was complete; that the aryl esterase was purified about 30-fold in near quantitative yield; that the hemoglobin was well resolved from the aryl esterase but was superimposed on the choline esterase; and that the protein concentration rose and fell suddenly at the expected boundary points, thus confirming the Kohlrausch conditions.

EXAMPLE II

This example is concerned with the separation of protein components in Japanese radish.

Preparation of Japanese Radish Sample

Six kg of Japanese radish roots were blenderized with 3 liters of distilled water. 7.15 liters of aqueous extract was obtained after the blended material was squeezed through cheesecloth and the extract was processed according to the method of Morita et al., Agric.Biol.- Chem. 25, 136 (1961), (which is incorporated herein by reference), through the 90% saturated ammonium sulfate step. The precipitate from the ammonium sulfate fractionation was dissolved in 100 ml. of 0.05 M pH 6.0 phosphate buffer and dialyzed against the same buffer. The dialysate (118 ml.) was passed through a CM-cellulose column (1.5" diam.×11" high) which had been equilibrated with 0.05 M pH 6.) phosphate buffer. The basic JRP-c was retained along with other basic proteins. The effluent fractions containing the acidic JRP-a were pooled. The pooled JRP-a fraction was concentrated 3 fold by placing it in a dialysis bag against dry Bio-Gel P-150 (a polyacrylamide gel filtration medium) for 5 hr. The concentrated preparation was then dialyzed for 12 hours against 15% (w/v) sucrose containing a buffer of 0.05 M HCl adjusted to pH 8.5 with Tris. The dialyzed sample was then used as the test sample.

The apparatus and test run procedures used in this test were exactly as set forth in Example I, with the exception that the Japanese Radish preparation was used in lieu of the horse serum, and in an amount sufficient to provide 15 milligrams total protein. The collected fractions were tested for protein content, peroxidase activity, and absorbance ratio (405 nm/276 nm).

Three separate visible bands of orangebrown color were present after steady-state conditions were achieved. Upon recovery and testing of fractions, it was clear that the central band was composed of highly purified peroxidase, as indicated by the absorbance ratio value of 3.20. As further evidence of this purification, this central band was recovered with 65-fold purification and 65% yield.

Having thus described the invention, what is claimed as new and desired to be secured by Letters Patent is:

1. In a Kohlrausch-regulated electrophoresis method wherein a mixture containing at least two macromolecular components to be separated is placed in a layer between a pair of physically distinct separate layers respectively including a leading ion and a trailing ion, the mobility of said leading ion being greater than that of said components, the mobility of said trailing ion being less than that of said components, and a direct current passed through said layers to effect separation of said components with said components being adjacent one another, the improvement which comprises employing as said trailing ion a non-aromatic, acyclic, substantially linear, at least partially water dispersible polymer which is compatible with said components, contains recurring ethylene oxide groups and at least one terminal group which is charge-bearing during said current passage, the mobility of said polymer being substantially independent of pH over a range of at least about 4 pH units, and with the mobility of the entirety of said trailing ion being less than the mobility of all of said components being separated.

2. The method as set forth in claim 1, said polymer having the formula:

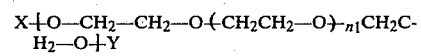

wherein X and Y are respectively selected from the group consisting of:
(a) organic substituents having up to six carbon atoms and terminating in a carboxyl group;
(b) loweralkyl substituents having from 1 to 4 carbon atoms;
(c) substituents of the formula

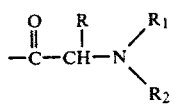

wherein R is an α amino acid side chain, $R_1$ is hydrogen or a loweralkyl having from 1 to 4 carbon atoms, inclusive, and $R_2$ is hydrogen, an amino acid or peptide;

(d) substituents of the formula

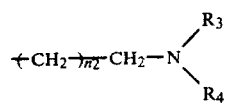

wherein $n_2$ is from 0 to 4, inclusive, and $R_3$ and $R_4$ are respectively taken from the group consisting of hydrogen and loweralkyl groups having from 1 to 4 carbon atoms, inclusive;

(e) substituents of the formula

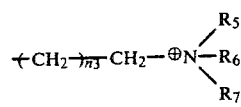

wherein $n_3$ is from 1 to 4, inclusive, $R_5$, $R_6$ and $R_7$ are respectively taken from the group consisting of hydrogen and loweralkyl groups having from 1 to 4 carbon atoms, inclusive;

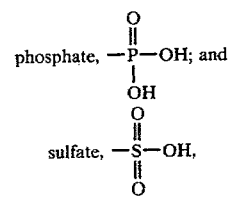

at least one of said X and Y being charge-bearing during said current passage, and wherein $n_1$ is sufficiently large to give the polymer a mass to charge ratio when fully ionized which is greater than that of said components to be separated.

3. The method as set forth in claim 1, at least one of said X and Y being of the formula

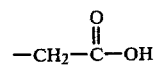

4. The method as set forth in claim 2, wherein $n_1$ ranges from about 100 to 150.

5. The method as set forth in claim 1, said polymer having a mobility of up to about $-1.3 \times 10^{-5}$ cm.$^2$/volt/sec. when fully ionized.

6. The method as set forth in claim 1, said components comprising proteins.

7. The method as set forth in claim 6, said mass to charge ratio of said polymer being at least about 3000 to 1.

8. The method as set forth in claim 1, including the step of recovering said components after said separation thereof.

* * * * *